United States Patent [19]
Skiffington

[11] Patent Number: 6,055,050
[45] Date of Patent: *Apr. 25, 2000

[54] PHOTOMETER AND TEST SAMPLE HOLDER FOR USE THEREIN, METHOD AND SYSTEM

[75] Inventor: Richard Skiffington, North Reading, Mass.

[73] Assignee: Charm Sciences, Inc., Malden, Mass.

[*] Notice: This patent is subject to a terminal disclaimer.

[21] Appl. No.: 09/342,310

[22] Filed: Jun. 29, 1999

Related U.S. Application Data

[63] Continuation of application No. 08/810,309, Feb. 28, 1997, Pat. No. 5,917,592.

[51] Int. Cl.[7] .................................................... G01N 21/01
[52] U.S. Cl. .................... 356/244; 356/246; 356/440; 422/82.05; 435/287.1
[58] Field of Search ................................... 356/244, 246, 356/243, 440; 250/576; 435/8, 4, 287.6, 21, 29, 30, 32, 34, 287.1, 287.7; 422/52, 82.05, 82.08; 436/172

[56] References Cited

U.S. PATENT DOCUMENTS

| | | |
|---|---|---|
| 3,714,445 | 1/1973 | Blachere et al. ............... 356/246 |
| 3,764,214 | 10/1973 | Heiss ............................ 356/246 |
| 4,213,703 | 7/1980 | Haunold et al. ............... 356/244 |
| 4,586,818 | 5/1986 | Lohr ............................. 356/244 |
| 4,730,933 | 3/1988 | Lohr ............................. 356/440 |
| 5,086,233 | 2/1992 | Stafford et al. ............... 356/244 |
| 5,139,745 | 8/1992 | Barr et al. .................... 422/82.05 |
| 5,917,592 | 6/1999 | Skiffington ................... 356/244 |

*Primary Examiner*—Hoa Q. Pham
*Attorney, Agent, or Firm*—Richard P. Crowley

[57] ABSTRACT

A photometer and a test sample holder, with the holder having a light-blocking, black upper section and a light-transparent, lower section test sample vial, for use with the photometer. The photometer includes an O-ring seal at an input, to the light measurement sample chamber, so on insertion of the holder, with a test sample to be detected in the test vial, the upper section blocks interfering light from the chamber.

11 Claims, 4 Drawing Sheets

PHOTOMETER AND TEST SAMPLE HOLDER FOR USE THEREIN, METHOD AND SYSTEM

REFERENCE TO PRIOR APPLICATION

This application is a continuation of U.S. Patent application Ser. No. 08/810,309 filed on Feb. 28, 1997, now U.S. Pat. No. 5,917,592, issued Jun. 29, 1999.

BACKGROUND OF THE INVENTION

Photometers and other instruments for detecting and measuring absorption or emission of light from a test sample can be useful measures of chemical and biological systems and changes, particularly in the determination of emitted light from test samples containing luminescent components.

There are a number of photometers for the measurement of light emission, wherein the test sample, whose light is to be determined, can be maintained at an acceptable optical temperature or other required conditions. Such a photometer usually requires a shutter assembly for sealing a test sample in the photometer, and a photosensitive device for the determination of the emitted light from the test sample. The assembly usually comprises a body having a sample chamber and a light path opening from the sample chamber to the photosensitive device. The body includes a means of mounting the sample chamber in relationship to the photosensitive device for the detection of the light transmitted from the sample chamber.

The assembly also requires a shutter assembly comprising an opaque housing to shield the photosensitive device from light transmitted from the sample chamber when in the closed position. Typically, the housing has an aperture for the communication between the photosensitive device, which may be a photomultiplier tube, and the light path from said sample chamber when the shutter is in an open position. A shutter or other means must be provided for securely closing the sample chamber to prevent the interference of external light when the device is in operation. One type of photometer for detecting and measuring luminescence in test materials is disclosed, for example, in U.S. Pat. No. 4,213,703, issued Jul. 22, 1980, entitled "Photometer with Stationary Sample Holder and Rotatable Shutter".

Photometer analyzers are typically included for use with multiple bioluminescent or chemiluminescent assay tests. One analyzer, known as a "Luminator®" (a trademark of Charm Sciences, Inc., of Malden, Mass.), is a portable analyzer which is adapted to detect emitted light and to interpret test assay results, and works in conjunction with a varying number of sample holders to determine and measure the presence of ATP, pesticides, phosphatase, and somatic cells; predict shelf life; and also to conduct general microbial quality tests for a wide variety of products. The device is capable of storing and sorting assay data in its memory, and transferring information to a display panel or printer or a computer system. The device also allows for on-site sample testing and for hard copy printouts or copy data management of test results at another location and time.

The analyzer is typically powered by a rechargeable, e.g. Lithium, battery pack or an AC-DC power supply. The Luminator® device includes a sample chamber with a turret having an entrance port, into which a test vial containing the test sample to be determined is inserted, and then the turret is rotated to a closed position to block external light from interfering with the photometer analysis. The turret is high positioned on the external top surface of the housing, typically to a clearance of at least ½ inch, in order to provide for a light-blocking seal, as allowing light into the sample chamber during the testing procedure would interfere with the test results. When the test results have been determined, the turret is rotated to the open position and the test sample vial removed.

The analyzer provides a user with the light emission count, in relative light units (RLU), of a test sample. The Luminator® photometer analyzer and its operation is described in greater detail in Charm's "Luminator-K Operating Instructions" Bulletin, (©1995 by Charm Sciences, Inc., Malden, Mass.), hereby incorporated by reference.

Generally, the test vial containing the sample employed in the test sample holder is a transparent or translucent vial, which permits the passage or emission of the emitted exposed light, for example, in a bioluminescent assay, and, for example, permits light transmission of from about 300 to 650 nanometers, which is visible light range. The test vial with the test sample therein may be separately inserted, or may be removed as a detachable component of a separate test sample holder device, such as an elongated tube, for example, a Pocketswab® device, (a registered trademark of Charm Sciences, Inc., of Malden, Mass.). The test vial with the test sample may be threadably removed from one end of the test sample holder and inserted as a separated test vial into the sample chamber, and then the sample turret closed.

One plastic, molded, test sample holder device is described in U.S. patent application Ser. No. 08/619,586, now U.S. Pat. No. 5,827,675, issued Oct. 27, 1998, (the National Phase, entered Mar. 26, 1996), of PCT application PCT/US96/00524, filed Jan. 2, 1996, and U.S. Design patent application Ser. No. 29/052,316, filed Apr. 2, 1996, now U.S. Pat. No. D.388,519, issued Dec. 30, 1997 both hereby incorporated by reference.

While such prior art photometers and test sample holders and methods are useful, it is desired to provide for an improved photometer analyzer with a reduced size sample chamber, without sacrificing the efficiency and performance of the photometer and the light blocking capability of the turret, and to provide a new and improved test sample holder suitable for use with the photometer.

SUMMARY OF THE INVENTION

The invention relates to a photometer and a test sample holder having a test sample vial for use with the photometer, and to a method and system of using the photometer and the test sample holder.

The invention concerns a photometer for use with a test sample holder, the holder having a light-blocking upper section and a light-transparent lower section test sample vial at the one end thereof, the sample vial holding a light-emitting test sample. The photometer is adapted for determination of emitted light from the test sample in the test vial in the sample chamber of the photometer.

The invention comprises a photometer and a test sample holder, alone and in combination. The photometer comprises a housing having a test sample vial holding chamber, an entrance port into the chamber for the sample vial, a photosensitive means, such as a photomultiplier tube, to receive emitted light from a test sample in the test vial in the chamber, and an optical light path between the chamber and the photosensitive means, with the test vial, when in use, disposed in said light path, electrical circuitry means to receive information from the photosensitive means, power supply means to supply electrical power to the electrical circuitry means, and means to receive and/or display information relative to the test sample or any controls, such as relative light units (RLU).

The photometer also includes a blocking means, typically disposed in the sample chamber. The blocking means is adapted to move between a light blocking position at an upper section of the sample chamber, when the test vial is not inserted in the entrance port, and a lower position, when said vial is positioned in the sample chamber for the collection of emitted light, and in the optical light path for transmission to the photosensitive device, and wherein the test sample holder, with the test vial secured thereon, functions to block the entrance port and external light from entering into the sample chamber. The blocking means is moved by the bottom of the test vial to a lower nonblocking position in the lower section of the chamber, when the test sample holder is inserted fully into the entrance port, and the test vial into the optical light path in the use position. The upper section of the test sample holder blocks interfering light from entering the entrance port, and the sample chamber during the test, and interfering with the determination of the emitted light from the test sample in the vial, when said vial is in the use position.

In one embodiment, the blocking means comprises a cap, e.g. a black plastic circular cap, secured to the end of a coiled spring. The cap is designed in dimension, e.g. circular, to fit against the inside of the sample chamber. The cap has a recessed lip about the top peripheral portion to provide for a close, light blocking seal within the sample chamber, and to allow it to rest at the top portion of the sample chamber against the lower portion of the entrance port chamber, at the point where the entrance port chamber meets the sample chamber.

The inserted test sample holder is held in position within the sample chamber by means of frictional engagement between the holder and a sealing gasket located near the top of the entrance port. Typically, the gasket may be composed of an elastomeric polymer and extend slightly radially inwardly from the periphery of the chamber inlet, so that the gasket may frictionally engage the sides of the inserted test sample holder to hold the test sample holder in the use position in the sample chamber, with the lower transparent test vial in the optical light path, to block light from entering the sample chamber during use, and to retain the light-blocking cap in a lower, spring-tensioned position. When the test sample holder is withdrawn after use, the tension-held cap then moves upwardly to seal the sample chamber by resting against the walls of the entrance port chamber, and again block the inlet of the sample chamber.

The test sample holder employed may be a standard elongated sample holder such as, but not limited to, a Pocketswab® device. Such test sample holders usually are composed of an upper section, with a cap, having a sample swab attached thereto to obtain a test sample, a hollow, tubular intermediate section to house the swab, and a lower section.

The lower section is comprised of a transparent test sample vial having one or a plurality of separate perforable or puncturable chambers, each containing one or more components (liquid or solids) required to complete the desired test with the test sample to provide, for example, a color change or emitted light, for example, from a luciferin-luciferase reaction. The lower transparent test vial receives the test sample collected with the components on the test swab as the test sample is longitudinally moved downwardly to pierce or otherwise contact the components. Thereafter, the swab tip is withdrawn from the test vial. Movement of the test swab may be accomplished by slidable or threadable movement of the cap and swab relative to the intermediate section. In other sample holders, contact of the test sample with the test components may be accomplished by separate mixing in the holder, the crushing of glass ampoules, or other means.

Usually, the test vial at one end and the entire holder is formed of a molded plastic, like an olefin resin, while the test vial is detachable, for example, by threads secured to the lower end of the intermediate section, and is made of a plastic, such as polypropylene, which is more transparent than the body of the sample holder, such as translucent polyethylene, to provide for transmission of the emitted light from the test sample. In some photometer analyzers, the test vial may be detached and used, capped or uncapped, in a photometer; however, the present invention permits the test vial to be used without the need to detach and insert the separated vial, and then to seal the vial in the sample chamber, such as with the heavy cast aluminum rotatable turret of the prior art. Usually, the test sample holder will include markings on the outer surface to indicate test swab position before sampling, after sampling, and after admixing. Generally, the test vial is threadably connected to the lower end of the intermediate section, having friction engaging lines to permit easy removal of the test vial and a diameter slightly less than the intermediate section, e.g., 1 cm. versus 1.5 cm. The holder is usually cylindrical, and in use, is designed on insertion to have the test vial in the sample chamber and the lower end of the intermediate section engaging the gasket at the sample chamber inlet or the outlet of the entrance port.

The test sample holder used with the analyzer photometer of the invention is designed, so that the upper section above the test vial is composed of a visible-light blocking material or treated, coated or otherwise comprised of a nontransparent material, so the holder in use in the photometer is held in position and blocks any interfering light into the sample chamber during measurement of luminescence from the test sample in the test vial. The test sample holders of the prior art are molded plastic holders of transparent or translucent polymers, which would be unacceptable for use in the present invention.

In one embodiment, the test sample holder, except for the test end, may be formed of a dark or a light-blocking or opaque plastic, such as by the incorporation of carbon black or light-blocking materials, pigments or chemicals in the plastic of the intermediate and end cap sections, or the use of carefully wrapped coatings or labels, or any combination of means to block interfering light from entering the inlet of the sample chamber in use. The preferred embodiment is the use of a black-colored, intermediate and end cap section on the Pocketswab® holder device. Bioluminescent test samples are usually tested between 300 and 650 nanometers, i.e. visible light range, however the holder may be designed to block any type or range of photoradiation depending on the test to be carried out.

Thus, the analyzer photometer of the invention provides an effective, smaller, less costly, lighter weight photometer without the requirement of a separate cap or turret, while the design of the photometer with the opaque light-blocking sample holder, which serves as a light-blocking cap when inserted in the entrance port, avoids the turret design and permits rapid tests without the need to remove the test vial from the holder. After testing, the test sample holder may then be disposed of without separating the test vial and avoiding contamination.

In the photometer, it is desirable that the sample chamber and photomultiplier tube (PMT) be arranged at the sample chamber exit to capture the emitted light of the test sample by a non-reflective, e.g. black color, and particularly where the photometer is to be a battery-operated, portable photometer, to be composed of black plastic.

The sample chamber, in one embodiment, includes emitted light-reflectant interior surrounding surface walls, so that all emitted light can be seen by the PMT. The sample chamber may include a metal tube, e.g. copper, with an exit aligned with the optical path to the PMT, and with the internal metal wall surface coated with a thin layer of a light-reflectant metal, like chromium, for better reflectance. The photometer may contain and include, like the Luminator® device, the standard optional large LED display panel in the housing, together with a touch board keyboard for the entering of information by a user, and optionally a printer or computer with a memory to receive, process, and collate the test data from the photometer.

Thus, the photometer analyzer of the invention provides for a photometer to measure emitted light from a test sample in a test vial without the requirement of a separate closure means to block interfering light, such as the heavy, cumbersome, rotatable light-blocking shutter closure.

The invention also provides for the test sample holder, with the detachable or nondetachable light transparent test vial at one end, to be inserted in the entrance port and to light-seal and block interfering light from the sample chamber during the test by having an upper section which snugly and frictionally fits into the entrance port in a sealing light arrangement with the upper section of the holder designed to block entering light from the sample chamber.

The invention will be described for the purposes of illustration only in connection with the preferred embodiment; however, it is recognized that changes, modifications and additions may be made to the preferred embodiment, by those persons skilled in the art, without departing from the spirit and scope of the invention.

DETAILED DESCRIPTION OF THE PREFERRED EMBODIMENTS

Figure 1:
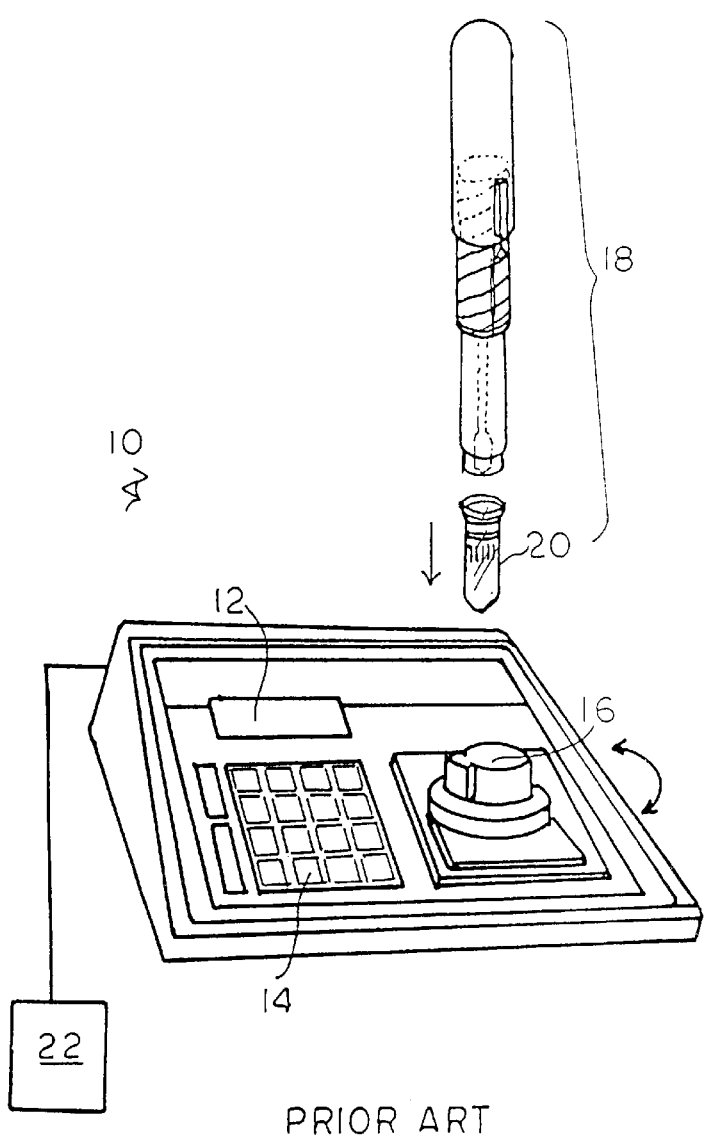
FIG. 1 is a perspective view of a prior art photometer analyzer with a prior art wholly transparent test sample holder.

In the drawings, FIG. 1 shows a prior art photometer 10 for detecting and measuring luminescence in test samples, with a light display panel 12, keyboard 14, and a lockable rotatable light-blocking turret 16. A prior art transparent test sample device 18 with test sample vial 20 detached thereon is shown in a position to be inserted into the photometer 10.

Figure 2:
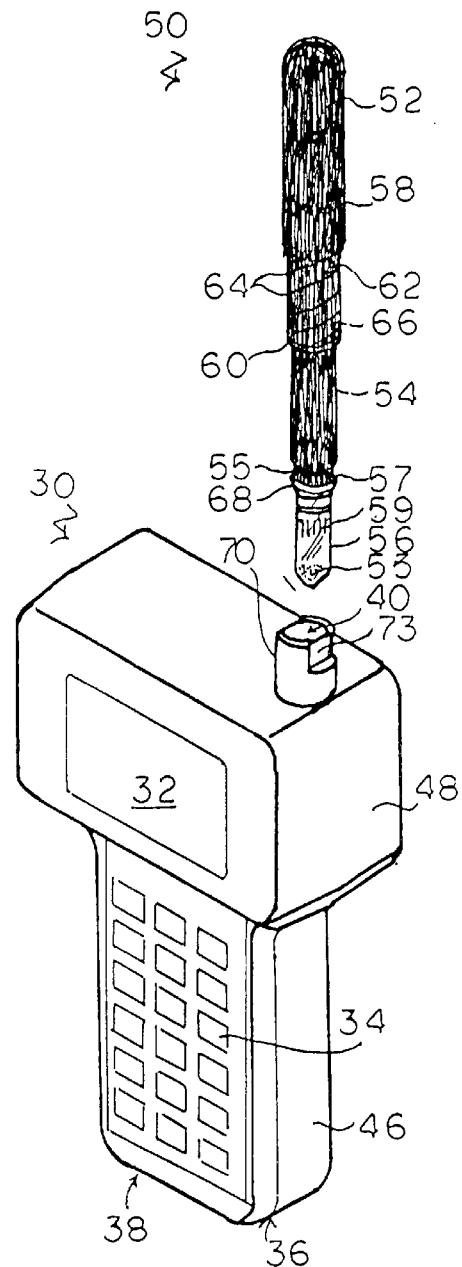
FIG. 2 is an exploded perspective view of the photometer and test sample holder of the invention.

FIG. 2 shows the portable photometer of the invention 30 with a new, light-blocking test sample holder 50. The photometer 30 has a light display panel 32, a keyboard 34, and a lower body section 46 and upper body section 48. The lower body 46 has an outlet 36 for a phone jack and a power outlet 38 at the bottom of the photometer. The upper body 48 has a sample holder entrance port 40 extending upwardly therefrom, which port has grip handles 73 on opposing sides of its upper portion.

In FIG. 2, the light blocking portable test sample holder 50 is shown in a position to be inserted into the sample holder entrance port 40. The holder 50 has a light-blocking upper cap 52, a light blocking intermediate tubular body section 54, and a lower, clear, test sample vial section 56. The upper cap 52 has a vertically extending raised line 58 thereon and internal threads on the lower surface (not shown). The intermediate light-blocking tube 54 has an upper and lower section, divided by a raised horizontal peripheral ridge 60. The upper section of tube 54 has threads 64 with an indicator arrow 62 and a vertical, indented, flat marking area 66 thereon. The lower section of tube 54 is smooth and rounded, with a bottom section of slightly reduced diameter 55. The translucent test sample vial 56, with test sample 53 therein, is detachably secured onto the lower section 55 of the intermediate tube 54 by a threaded top section 57, which threads into an inner threaded portion (not shown) on the lower section 55. Vertical grip ridges 59 provide for ease in threadably securing the test sample vial 56, and horizontal ridge 68 on the test vial provides for a stopping means for the threaded section 57. FIG. 2 shows an optional protective dust cap 71 for the entrance port 40.

Figure 3:
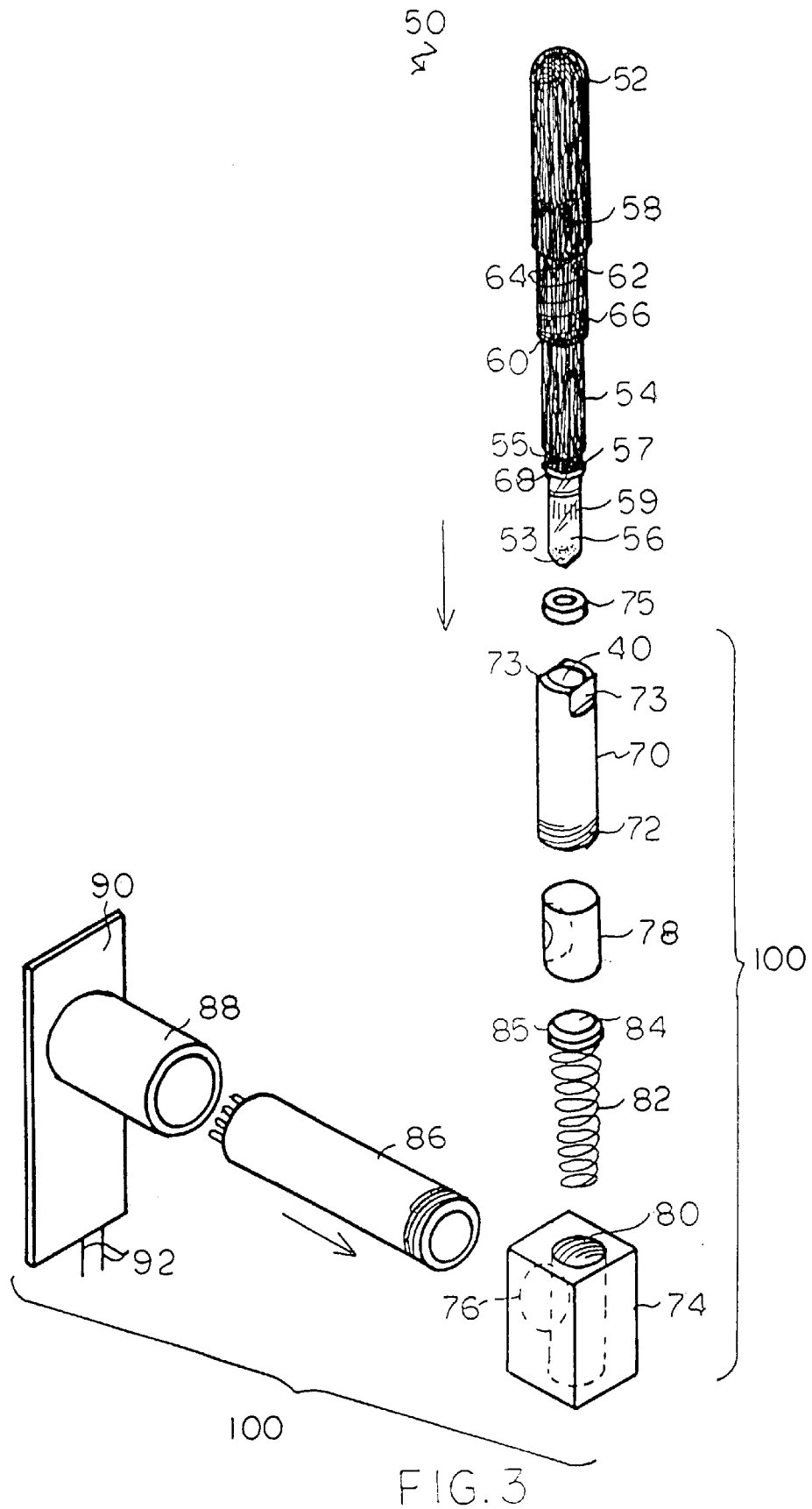
FIG. 3 is an exploded perspective view of the sample chamber unit of the photometer and the test sample holder of FIG. 2.

FIG. 3 shows the sample in an exploded perspective view 100, internal components of the photometer 30 with the test sample holder 50 ready to be inserted in entrance port 40. An elastomeric O-ring 75 is inserted into the top portion of an entrance tube 70, to permit the insertion of and for retention therein of the test sample holder 50 with vial 56 into the entrance port 40. The entrance tube 70 has a lower threaded end 72 and an upper end with grip handles 73 to facilitate the threading of the tube into the upper threaded portion 80 of the sample chamber block 74. A chromium plated copper internal sample chamber tube 78 is inserted within sample chamber block 74. A compression spring 82 with a black plastic light blocking cap 84 is inserted within the internal tube 78. The cap 84 has a raised peripheral ridge 85 thereon to sealably block the entrance port 40 and to prevent any external light from entering therein.

The sample chamber block 74 has a threaded outlet 76 on one side for the threadable insertion of a photomultiplier 86 therein. The photomultiplier 86 has a one threaded end and another end connected to the electrical circuitry of the sample chamber unit. The electrical circuitry has a photomultiplier receiver 88 attached to a receptor panel 90, which panel has electrical connecting wires 92 to the electrical power circuitry.

Figure 4:
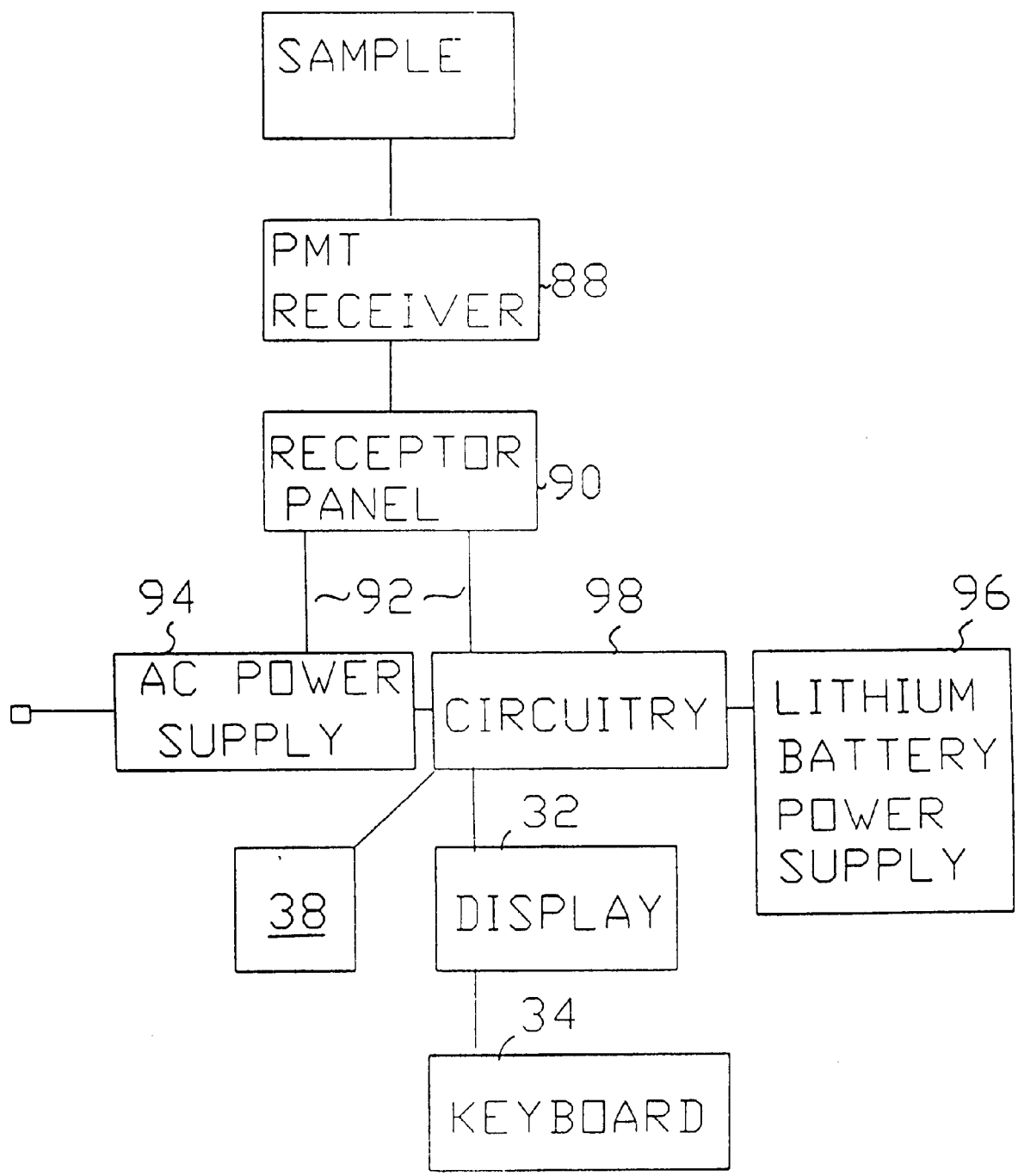
FIG. 4 is a block schematic diagram of the photometer of FIG. 2.

FIG. 4 shows a block schematic diagram of the photometer 30. The diagram shows the photomultiplier 88 connected to the receptor panel 90, with electrical connectors 92 extending into the circuitry board 98 and the AC power supply 94. The circuitry board 98 is also connected to the lithium battery power supply 96, the display 32, the AC power supply 94, and the download to an outside power supply 38. A keyboard 34 is connected to and operates the light display board 32.

Figure 5:
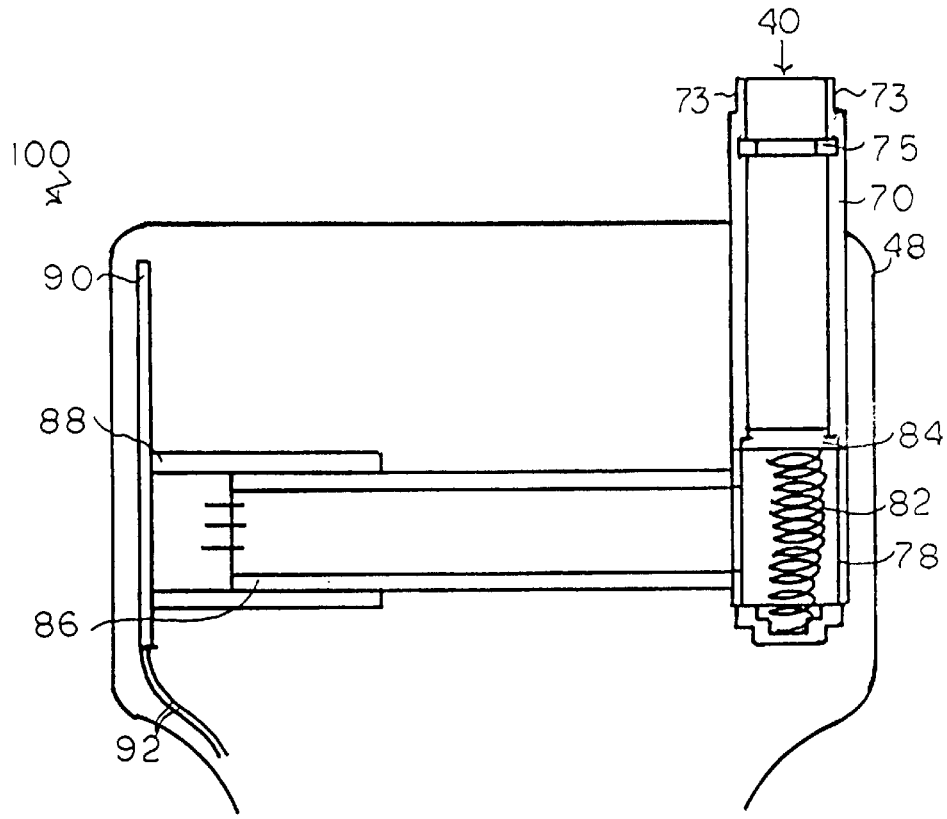
FIG. 5 is a fragmentary, enlarged sectional view of the sample chamber and test sample holder of FIG. 3 in a nonuse position.
Figure 6:
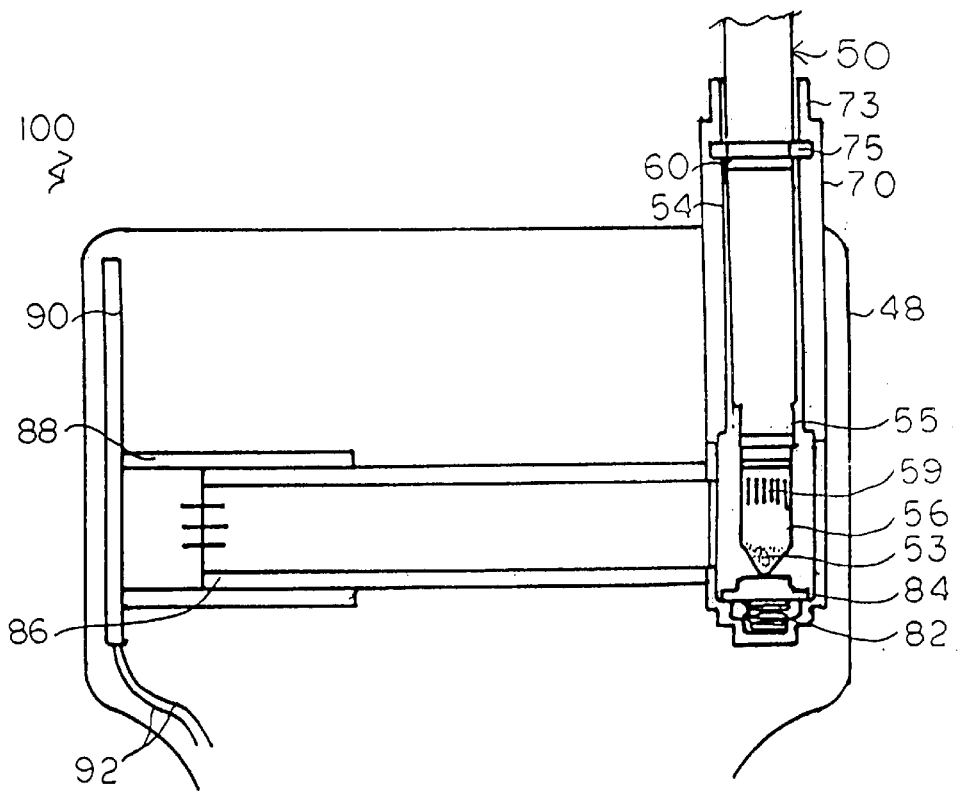
FIG. 6 is a fragmentary, enlarged sectional view of the sample chamber and test sample holder of FIG. 3 in a use position.

FIGS. 5 and 6 show the sample chamber unit 100 of the photometer 30 in an enlarged, sectional fragmentary view, with FIG. 5 in a nonuse position and FIG. 6 in a use position with the test sample vial 56. FIG. 5 shows the entrance tube 70 with side grips 73 and O-ring 75 inserted therein. The sample chamber internal tube 78 is within the sample chamber block 74 to define the sample chamber and opens to the sample chamber outlet 76. The compression spring 82 and plastic light-blocking cap 84 are shown in their relaxed, blocking position over the upper threaded end opening 80 of the sample chamber.

The photomultiplier tube 86 is threadably attached to the sample chamber outlet 76 at one end, and at the other end is inserted into the photomultiplier receiver 88 secured to the receptor panel 90. Connecting wires 92 extend from the panel 90 into the lower body 46 of the photometer, where the circuitry is contained.

FIG. 6 shows the sample chamber unit 100 in a use position, with the test sample 53 in a test sample vial 56 inserted within the unit 100 and secured by the rubber O-ring 75, with the seal of the O-ring and the raised horizontal ridge 60 of test sample holder 50 preventing external light penetration into the sample chamber. The test sample vial 56, is shown depressing the cap 84 and compressing the spring 82, allowing the test sample vial 56 with the test sample 53 to be in a position to allow the light emitted by the test sample 53 to be analyzed.

In use, the test sample holder 50 and photometer 30 of are transported as a unit to a location for use in obtaining and analyzing a test sample. To obtain a sample, the upper cap 52 of the light-blocking test sample holder 50 is twisted upward and threadably removed from the intermediate tube 54. A swab (as shown in FIG. 1), that has been inserted into the interior of the cap 52 is contacted with the test surface or material to be tested (not shown).

After the test sample is obtained, the cap 52 with the swab and test sample thereon is returned to the test sample holder intermediate tube 54, and threadably secured to the unit. Next, the cap 52 is threadably twisted down to push the swab down through tube 54 into the test sample vial 56, where the swab punctures the puncturable seals located in the test sample vial 56, which seals cover compartments that contain reactants or other chemicals to be admixed with the swab-collected test sample, to admix a test sample 53 that can be measured and analyzed by the photometer 30. After the test sample is admixed, the swab is then partially retracted by the threadable twisting upward of the cap 52.

The test sample holder 50, with the attached sample vial 56 having the admixed test sample 53 therein is then inserted into the entrance port 40 of the photometer analyzer 30. Upon insertion, the test sample vial 56 depresses the light-blocking cap 84 and compresses the tension-coiled spring 82 until the vial 56 is in position within the sample chamber, to have the light emitted from the test sample 53 to be accurately read by the light receiver 88 at the end of the photomultiplier tube 86. The horizontal ridge 60 on the intermediate tube 54 of the test sample holder 50 is frictionally engaged with the O-ring 75 within the entrance tube 70 to secure its position within the sample chamber, and to block light from entering the chamber.

Once secured within the chamber, the light emitted from the sample 53 is reflected in the chromium-plated internal chamber 78 and passes through the photomultiplier tube 86 to light receiver 88. The receiver 88 then transmits the information to the electric circuitry 98 by means of receptor panel 90 and electrical wires 92. The electric circuitry 98 is housed in the lower body section 46 of the housing, together with a keyboard 34 and AC power supply 94 and Lithium battery power supply 96. The circuitry is further connected to a download power supply 38 and a telephone outlet jack 36. The circuitry is also connected to a display panel 32 located in the upper body section 48 of the housing. After the sample is analyzed, the test sample holder 50 is withdrawn from the entrance tube 70 and may be disposed of by the user without separating the test vial 56 and thus avoiding contamination.

While the drawings illustrate a black light-blocking test sample holder 50, it should be recognized that other light-blocking colors, or combinations of colors, may be used as desired to provide the same result. Further, light-blocking chemicals, such as benzoates, may be added to the light-blocking components 52 and 54 to allow for the use of translucent or colored plastic material as desired, or any combination thereof.

What is claimed is:

1. A photometer for use with a test sample holder having an integral light-blocking section and a light-transparent test sample vial at one end thereof, said sample vial to hold a light-emitting test sample, said photometer adapted for the determination of emitted light from said test sample in said vial, and which photometer comprises:

a) a housing having a test sample vial holding chamber, an entrance port into said chamber for said sample vial, a photosensitive means to receive emitted light from said test sample in said test sample vial, an optical light path between said chamber and said photosensitive means, an electrical circuitry means to receive information from said photosensitive means, a power supply means to supply electrical power to said electrical circuitry means, and a means to display information relative to said test sample; and b) a fixed engaging and sealing means positioned within the holding chamber to engage and seal against an exterior surface of the light-blocking section of said sample holder, with said test vial in a use position, to block external interfering light from said sample-holding chamber.

2. The photometer of claim 1 wherein said engaging and sealing means comprises a frictional gasket.

3. In combination, the photometer of claim 1 and a test sample holder having an integral, light-blocking, colored upper section and a light transparent lower section of a test sample vial to contain a test sample which emits light, to be determined by said photometer.

4. The combination of claim 3 wherein said test sample holder includes a longitudinal, movable upper section with a test sample collecting swab, a hollow, light-blocking middle section, and a lower test sample vial containing separate packaged components to contact said swab-collected test sample, wherein said test sample, contacted with said components, emits light for measurement by said photometer.

5. The combination of claim 3 wherein said test sample holder is composed of molded plastic, and characterized by a black, visible light-blocking color and only said test sample vial comprises a light-transparent material.

6. The photometer of claim 1 which is free of any externally positioned moveable means to seal an inlet of the sample-holding chamber from an external interfering light.

7. An elongated, generally cylindrical test sample holder having a light-transparent test sample vial at the one end thereof to contain a test sample, and test components to provide emitted light to be measured by a photometer, and having an integral, upper light-blocking section at the other end, said sample holder adapted to have the one end inserted into a sample-holding chamber of a photometer and the other end to block visible light from entering said sample chamber.

8. The sample holder of claim 7 which includes an upper section composed of a threadable longitudinal movable cap with a test sample collecting swab, and a hollow, tubular middle section, said cap and middle section having a dark-colored, light-blocking component in said plastic material.

9. The sample holder of claim 7 wherein said light-transparent sample test vial contains in separated, swab-puncturable compartments, components required to carry out a test on said collected test sample.

10. A method of measuring in a photometer, light from a test sample in a light-transparent test sample vial at one end of a test sample holder, which holder integrally includes a light-blocking upper section having a peripheral, exterior side surface to be sealed, which method comprises:

a) inserting the test sample holder into an entrance port of a photometer having a sample-holding chamber with an inlet;

b) placing the transparent test vial with the test sample into an optical light path in the sample-holding chamber;

c) blocking external, interfering light from entering the inlet of the sample chamber by engaging and sealing of the peripheral, exterior side surface of the upper light-blocking section of the test sample holder; and d) measuring the light in or from the test sample in the test vial.

11. A photometer adapted for use with a test sample holder, to measure luminescence from a test sample, which comprises a photometer having a sample-holding chamber to receive therein a transparent test vial of a test sample holder with a test sample to be measured, the test sample holder having an upper light-blocking section and the photometer having an entrance port and sample-holding chamber with an inlet and an interior side wall with a peripheral groove therein, and an optical-electrical means to define an optical light path and to measure the luminescence of the test sample in the light path in the sample-holding chamber, and which photometer includes a fixed, light-blocking engaging and sealing gasket positioned in the groove of the sample-holding chamber, to engage and seal against an exterior surface of the light-blocking section of the test sample holder, to block external light from said chamber.

* * * * *